United States Patent [19]

Hayakawa et al.

[11] Patent Number: 6,043,262
[45] Date of Patent: *Mar. 28, 2000

[54] THIFLUZAMIDE WITH IMPROVED EFFICACY

[75] Inventors: Norihito Hayakawa; Masatoshi Baba, both of Funabashi; Norihiro Suwa, Narashino; Kazuhiro Yamagishi, Tokyo, all of Japan

[73] Assignee: Rohm and Haas Company, Philadelphia, Pa.

[ * ] Notice: This patent is subject to a terminal disclaimer.

[21] Appl. No.: 09/125,988

[22] PCT Filed: Feb. 28, 1997

[86] PCT No.: PCT/JP97/00613

§ 371 Date: Nov. 24, 1998

§ 102(e) Date: Nov. 24, 1998

[87] PCT Pub. No.: WO97/31908

PCT Pub. Date: Sep. 4, 1997

[30] Foreign Application Priority Data

Feb. 28, 1996 [JP] Japan ..................................... 8-065138

[51] Int. Cl.$^7$ ........................... A01N 43/78; C07D 277/54
[52] U.S. Cl. ............................................. 514/365; 548/200
[58] Field of Search .............................. 514/365; 548/200

[56] References Cited

U.S. PATENT DOCUMENTS

| 5,045,554 | 9/1991 | Alt et al. ................................. 514/365 |
| 5,837,721 | 11/1998 | Hayakawa et al. ..................... 514/365 |
| 5,886,188 | 3/1999 | Bryman et al. .......................... 548/200 |

FOREIGN PATENT DOCUMENTS

| 2184680 | 7/1990 | Japan . |
| 8291009 | 11/1996 | Japan . |

*Primary Examiner*—Frederick Krass
*Attorney, Agent, or Firm*—Roylance, Abrams, Berdo & Goodman, L.L.P.

[57] ABSTRACT

The present invention provides thifluzamide which has changed its crystalline form, its preparation method, and a pesticide composition containing thifluzamide as its effective ingredient. The rate of dissolution of the thifluzamide obtained is high and the pesticide compounds containing it has improved efficacy.

20 Claims, 2 Drawing Sheets

1

THIFLUZAMIDE WITH IMPROVED EFFICACY

FIELD OF THE INVENTION

The present invention relates to N-(2,6-dibromo-4-trifluoromethoxyphenyl)-2-methyl-4-trifluoromethyl-5-thiazolecarboxyamide (general name: thifluzamide) with a transformed crystalline form, its preparation method, and a pesticide composition containing thifluzamide as an effective ingredient.

BACKGROUND OF THE INVENTION

Thifluzamide is a compound that has high fungicide activity against rice sheath blight.

Because the time to use a chemical against rice leaf spot withering disease in the cultivation of rice plant is when the rice field is covered with a lesser amount of water, the rate of release and diffusion of effective ingredient affects the controlling effect significantly. However, since water solubility of thifluzamide is extremely low like 1.6 mg/l (20° C.), it is desirable to develop a method that increases the rate of its release in water and improves its efficacy.

DISCLOSURE OF THE INVENTION

The present inventors have discovered that thifluzamide changes its crystalline form when crystallized from a mixture of water and a solution prepared by dissolving the thifluzamide synthesized by a conventional preparation method in organic solvent and that releasability of thifluzamide in water is improved by preparing a pesticide composition using the thifluzamide with transformed crystalline form.

The present invention relates to the following thifluzamide and a process for preparing them.

(1) Thifluzamide showing endothermic peak at 175–180° C. by differential scanning calorimeter analysis and having no other peak at less than that temperature.

(2) Thifluzamide showing a peak at 2θ=17.68, 20.04, 23.04, 28.88 and 29.52 by powder X-ray diffraction analysis.

(3) A process for preparing thifluzamide described in (1) or (2) comprising admixing the solution of thifluzamide dissolved in an organic solvent with water to crystallize thifluzamide.

(4) A process of (3) incorporating the solution of thifluzamide dissolved in an organic solvent into water to crystallize thifluzamide.

(5) A process of (3) incorporating water to the solution of thifluzamide dissolved in an organic solvent to crystallize thifluzamide.

(6) A process of (3), (4), or (5) wherein the water solubility of an organic solvent at 20° C. is 10 or more parts by weight of water solution.

(7) A process of (3), (4), or (5) wherein an organic solvent is miscible with water in any ratio.

(8) A process of (3), (4), or (5) wherein organic solvent is one or more solvent selected from the group consisting of alcohols, ketones, ethers, esters, nitrites, N-alkyl pyrrolidones, N,N-dimethyl-formamide or dimethylsulfoxide.

(9) A pesticide composition containing thifluzamide of (1) or (2) as an effective ingredient.

(10) A pesticide composition containing thifluzamide prepared by the process of (3), (4), (5), (6), (7), or (8) as an effective ingredient.

BEST MODE OF PRACTICING INVENTION

Figure 1:
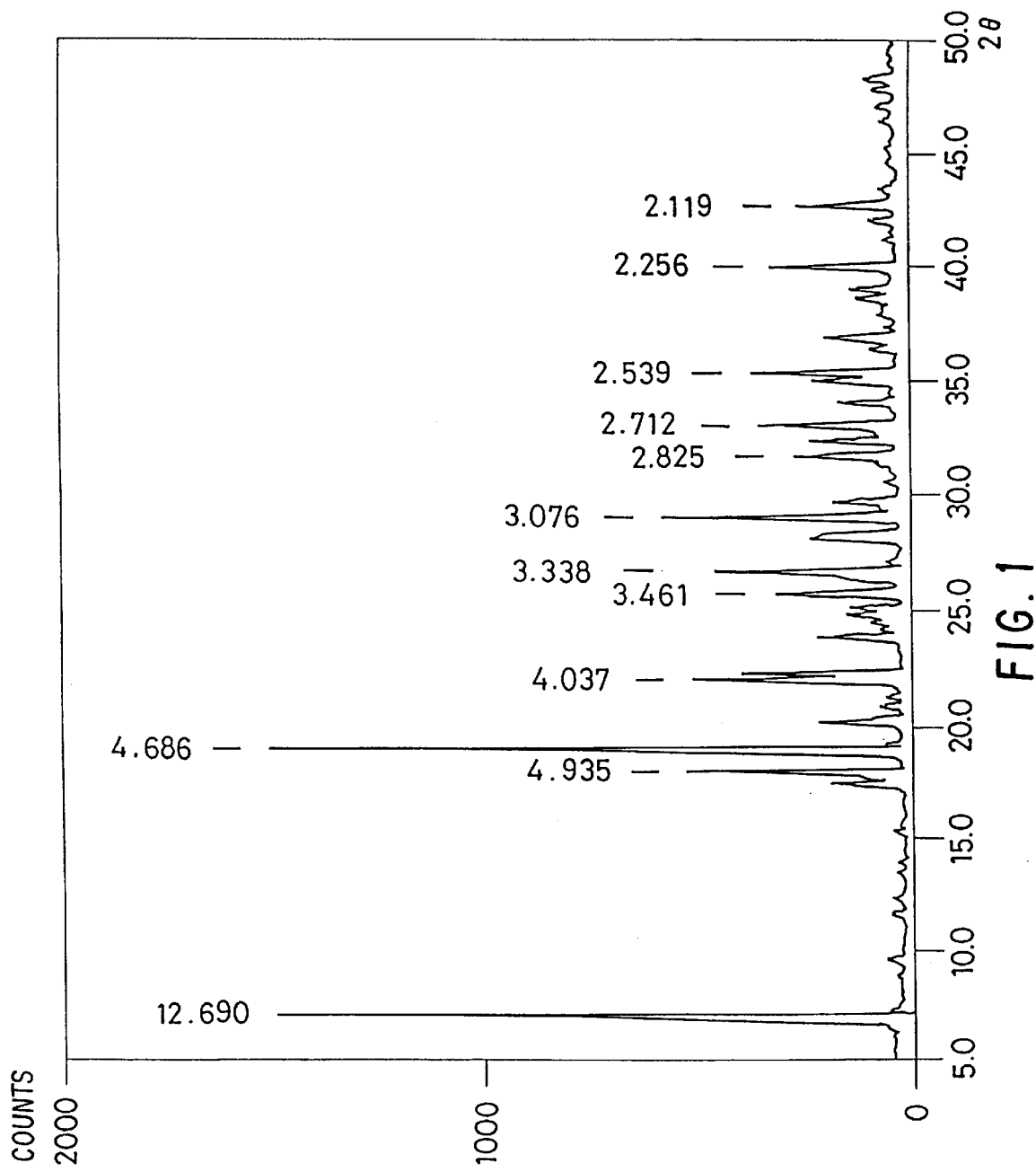
FIG. 1 shows powder X-ray diffraction profile of α-crystalline thifluzamide obtained in the Referential Example.

Melting point of thifluzamide is known to be 177.9–178.6° C. (Pesticide Manual, 1994). However, the thifluzamide synthesized in the Referential Example to be stated later shows an endothermic peak in the vicinity of 178° C. by differential scanning calorimetry (DSC), and it shows an additional endothermic peak of 2.0–2.5 cal/g in the vicinity of 161° C. In powder X-ray diffraction analysis, it shows a diffraction profile shown in FIG. 1. Thifluzamide of such crystalline form is called "α-crystal".

The thifluzamide of the present invention with a transformed crystalline form has a crystalline structure different from the α-crystalline form as shown by powder X-ray diffraction analysis and DSC analysis of the thifluzamide obtained in Example 1. Specifically, it shows an endothermic peak only in the vicinity of 178° C. by DSC and does not show endothermic peak at less than that temperature. And, in powder X-ray diffraction analysis, the thifluzamide shows a diffraction profile shown in FIG. 2 and shows diffraction peaks at 2θ=17.68, 20.04, 23.04, 28.88 and 29.52. Thifluzamide having such crystalline form is called "β-crystal".

The β-crystalline thifluzamide of the present invention is prepared by admixing the solution of thifluzamide dissolved in organic solvent with water to crystallize. The thifluzamide can be obtained by incorporating the solution of thifluzamide dissolved in organic solvent into water or by incorporating water to the solution of thifluzamide dissolved in organic solvent.

Even though there is no particular restriction about the organic solvents that can be used in the present invention, desirably the water solubility of organic solvent at 20° C. in aqueous solution is 10 or more parts by weight, and more desirably it is an organic solvent that is miscible with water in any ratio. For example, one or more solvents selected from alcohols, ketones, ethers, esters, nitriles, N-alkyl pyrrolidones, N,N-dimethyl formamide and dimethyl sulfoxide are preferable. Suitable organic solvents useful in the present invention, but are not limited to: alcohols, such as allyl alcohol, isobutyl alcohol, isopropyl alcohol, ethanol, tetrahydrofurfuryl alcohol, s-butanol, t-butanol, furfuryl alcohol, propagyl alcohol, 1-propanol, methanol, 3-methyl-1-pentyne-3-ol, ethyleneglycol, ethyleneglycol diacetate, ethyleneglycol diglycidyl ether, ethyleneglycol monoacetate, ethyleneglycol dimethyl ether, ethyleneglycol monoethyl ether, ethyleneglycol monoethyl ether acetate, ethyleneglycol monobutyl ether, ethyleneglycol monomethyl ether, ethyleneglycol monomethyl ether acetate, ethyleneglycol monomethoxy methyl ether, ethylene chlorohydrin, glycerin, glycerin 1,3-dimethyl ether, 2-chloro-1,3-propanediol, diethyleneglycol, diethyleneglycol ethylmethyl ether, diethyleneglycol chlorohydrin, diethyleneglycol diacetate, diethyleneglycol diethyl ether, diethyleneglycol dimethyl ether, diethyleneglycol monoethyl ether, diethyleneglycol monoethyl ether acetate, diethyleneglycol monobutyl ether, diethyleneglycol monoethyl ether, dipropyleneglycol, dipropyleneglycol monoethyl ether, dipropyleneglycol monomethyl ether, tetraethyleneglycol, triethyleneglycol, triethyleneglycol monoethyl ether, triethyleneglycol monomethyl ether, trimethyleneglycol, 1,3-butanediol, 1,4-butanediol, propyleneglycol, propyleneglycol monoethyl ether, propyleneglycol monomethyl ether, and 1,5-pentanediol; ethers and acetals, such as diethyl ether, 1,4-dioxane, dipropyl ether, dimethyl ether, tetrahydropyrane, tetrahydrofuran, furfural, and methylal; ketones, such as acetone, diacetone alcohol, and methylethyl ketone; esters, such as ethyl formate, methyl formate, ethyl acetate, methyl acetate, ethyl lactate, methyl lactate, and γ-butyrolactone; carboxylic acids, such as isobutyric acid, formic acid, acetic acid, and dichloroacetic acid; nitriles, such as acetonitrile and propionitrile; N-alkyl pyrrolidones, such as 2-pyrrolidone, N-methyl-2-pyrrolidone, N-vinyl-2-pyrrolidone, N-ethyl-2-pyrrolidone, N-(2-hydroxyethyl)-2-pyrrolidone, N-cyclohexyl-2-pyrrolidone, N-isopropyl-2-pyrrolidone, N-(n-butyl)-2-pyrrolidone, N-(t-butyl)-2-pyrrolidone, N-(3-hydroxypropyl)-2-pyrrolidone, N-(2-methoxyethyl)-2-pyrrolidone, and N-(3-methoxypropyl)-2-pyrrolidone; others material, such as allylamine, N-ethyl ethanolamine, ethylenediamine, diethylamine, N,N-dimethylformamide, N,N,N',N'-tetramethyl ethylenediamine, triethylamine, trimethylamine, pipecoline, piperidine, propylenediamine, hexamethyl phosphortriamide, monoethanolamine, and dimethylsulfoxide.

Preferred are isopropyl alcohol, ethanol, 1-propanol, methanol, ethyleneglycol, ethyleneglycol monoethyl ether, ethyleneglycol monobutyl ether, ethyleneglycol monomethyl ether, ethyleneglycol monomethoxymethyl ether, diethyleneglycol, 1,4-butanediol, propyleneglycol, propyleneglycol monoethyl ether, propyleneglycol monomethyl ether and so on for alcohols; tetrahydrofuran and tetrahydropyrane for ethers; acetone, diacetone alcohol, and methylethyl ketone for ketones; acetonitrile and propionitrile for nitriles; and methyl lactate, N-methyl-2-pyrrolidone, N,N-dimethylformamide, and dimethyl-sulfoxide for other materials.

More preferred are methanol, ethanol, acetone, tetrahydrofuran, acetonitrile and N-methyl-2-pyrrolidone.

Any conditions under which the thifluzamide can be crystallized immediately after adding thifluzamide solution to water or after adding water to the thifluzamide solution can be employed to control crystallization in water in the present invention, and there is no particular restriction about the temperature of the thifluzamide solution, rate of addition of water to the thifluzamide solution, water temperature, quantity of water, or agitation speed, etc.

For example, if a solvent such as acetone or methanol that can dissolve thifluzamide at room temperature is selected, a complete transition to β-crystalline form can take place easily when thifluzamide solution is added into water at room temperature to cause crystallization, and thus it will be easy to control the production condition and be useful from the aspect of stabilizing the quality of the product.

There is no particular restriction about the type of pesticide composition that employs β-crystalline thifluzamide as the effective component in the present invention, for example, powder, wettable powder, pellet, tablet, water dispersible glanule and suspension can be mentioned. Each of them can be prepared by an ordinary method. As to the additives other than the β-crystalline thifluzamide to be added in the pesticide composition of the present invention, there is no particular restriction.

Furthermore, other effective ingredients than β-crystalline thifluzamide may be added as the effective ingredients in the pesticide composition of the present invention.

Antimicrobial efficacy and the ability to release thifluzamide into water from the pesticide composition comprising the β-crystalline thifluzamide obtained by the present invention as the effective ingredient are better than the case that employs α-crystalline thifluzamide.

The pesticide composition of the present invention may comprise both α-crystalline thifluzamide and β-crystalline thifluzamide. However, from the viewpoint of improvement of releasability into water, the mixing ratio of β-crystalline form is preferably 20–100%, more preferably 50–100%.

EXAMPLES

The present invention is explained embodically by the Referential Example, Examples, and Examples of Tests illustrated below. However, the present invention is not limited only to those examples. "Parts" in the following Examples and Comparative Examples mean "parts by weight". DSC and powder X-ray diffraction analysis shown in the Reference Example and Examples were performed under the test conditions illustrated below.

| DSC Analysis (in air) | |
| --- | --- |
| Equipment | DSC-3100, by Mac Science Co. |
| Weight of sample | 3 mg |
| Sample pan | Aluminum |
| Sampling rate | 1.0 second |
| Rate of temperature elevation | 5.0° C./minute |
| Powder X-ray diffraction analysis | |
| Equipment | JDX-8200T, by Nippon Denshi K.K. |
| Target | Cu 2θ = 5°–50° |
| Step angle | 0.040 |
| Counting time | 0.5 second |
| Tube voltage | 30.0 kV |
| Tube current | 100.0 mk |

Referential Example
Synthesis of α-Crystalline Thifluzamide

2-Methyl-4-trifluoromethyl-5-chlorocarbonyl thiazole 6.47 g and 2,6-dibromo-4-trifluoromethoxy aniline 8.91 g were added in acetonitrile 16.8 ml, and they were heated to reflux for 6.5 hours. Solvent was removed from the reaction mixture by distillation under a reduced pressure, and then ethyl acetate 420 ml and water 300 ml were added and they were agitated. After standing calmly, the ethyl acetate layer was collected, and washed with water, saturated sodium bicarbonate solution, and water (300 ml each) in succession. Then, after drying over anhydrous sodium sulfate, solvent was removed by distillation under a reduced pressure, to obtain thifluzamide 13.9 g.

The starting materials, 2-methyl-4-trifluoromethyl-5-chlorocarbonyl thiazole and 2,6-dibromo-4-trifluoromethoxy aniline, were synthesized according to the procedures described in the Example 1 of Japanese Patent Publication (kokai) No. 184680/90.

The thus-obtained crystal showed an endothermic peak of 2.1 cal/g in the vicinity of 161° C. and another endothermic peak of 9.0 cal/g in the vicinity of 178° C. by DSC analysis. And, as illustrated in FIG. 1, the relative peak intensity at 2θ=17.7° was I/Io=12 and the relative peak intensity at 2θ=23.0° was I/Io=11. The crystal obtained in this Referential Example was called a "α-crystal".

Example 1
Synthesis of β-Crystalline Thifluzamide

α-Crystalline thifluzamide 15 g obtained in the Reference Example was dissolved in acetone 30 g at room temperature, and this solution was added dropwise from a dropping funnel into distilled water 500 ml in a 1 liter beaker, with constant agitation at a speed of 300 rpm, over 5 minutes period. The substance which was crystallized in water was collected by filtration under reduced pressure through a 1 μm paper filter and washed with water 500 ml. The obtained thifluzamide crystal was dried under a reduced pressure at about 60° C. for 2 hours.

Figure 2:
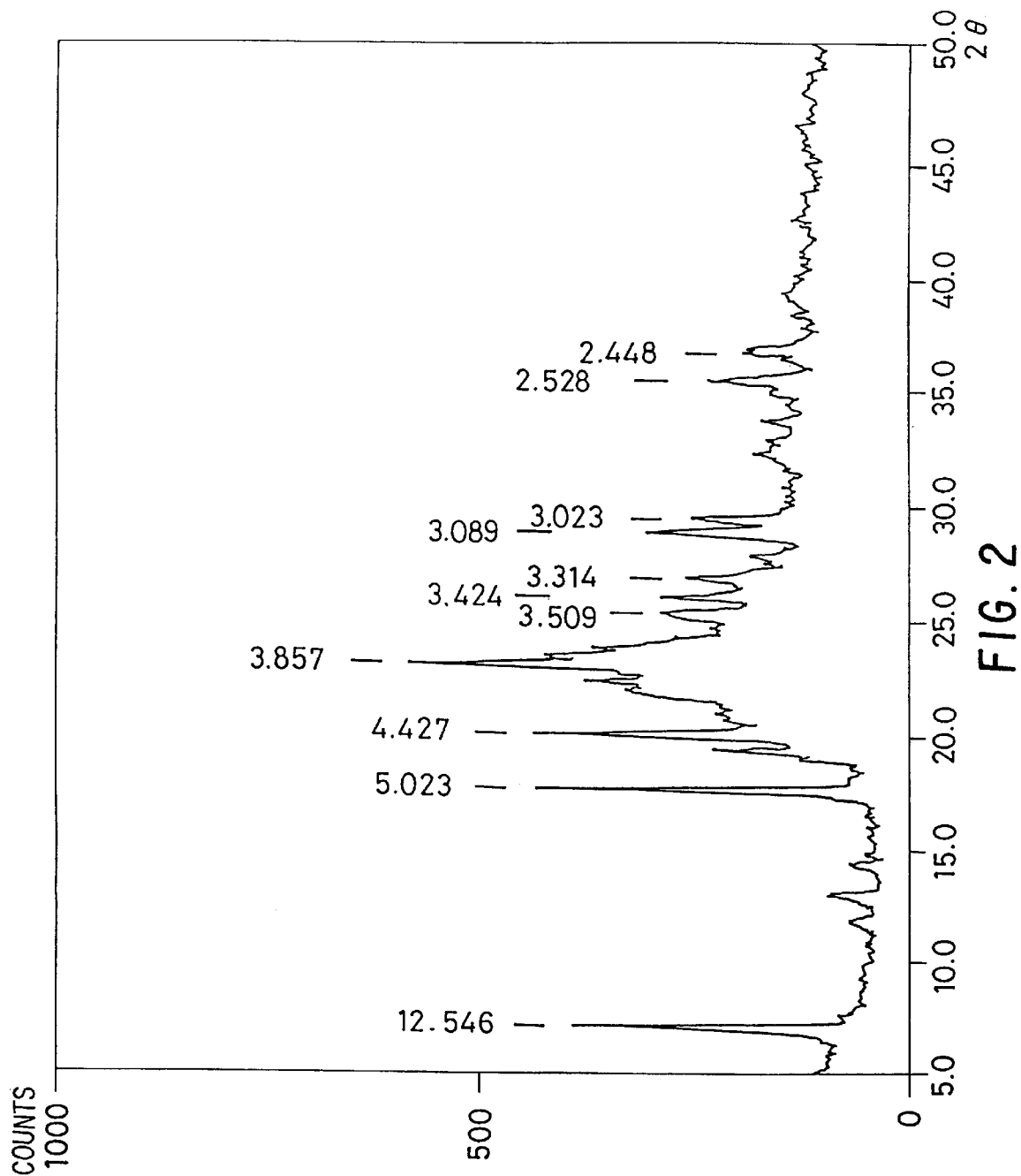
FIG. 2 shows powder X-ray diffraction profile of β-crystalline thifluzamide obtained in the Example 1.

The obtained crystal showed an endothermic peak of 10.2 cal/g in the vicinity of 178° C., but it shows no endothermic peak in the vicinity of 161° C. by DSC. The powder X-ray diffraction profile, as illustrated in FIG. 2, showed a peak at 2θ=17.68, 20.04, 23.04, 28.88 and 29.52 and showed a relative peak intensity of I/Io=75 at 2θ=17.6° and a relative peak intensity of I/I°=100 at 2θ=23.0°, and thus its crystalline form was different from that of α-crystal. The crystal obtained in the present Example was called "β-crystal".

Example 2
Synthesis of β-Crystalline Thifluzamide

Procedure of Example 1 was repeated, except using methanol 60 g to replace acetone 30 g. Crystal of the obtained thifluzamide was found to be a β-crystal by DSC and powder X-ray diffraction analysis.

Example 3
Synthesis of α+β Mixed Crystalline Thifluzamide

Procedure of Example 1 was repeated, except using tetrahydrofuran 30 g to replace acetone 30 g. Crystal of the obtained thifluzamide was found to be a mixture of α- and β-crystals by DSC and powder X-ray diffraction analysis.

Example 4
Synthesis of α+β Mixed Crystalline Thifluzamide

Procedure of Example 1 was repeated, except using N-methyl pyrrolidone 15 g to replace acetone 30 g. Crystals of the obtained thifluzamide were found to be a mixture of α and β-crystals by DSC and powder X-ray diffraction analysis.

Example 5
Pellet 1 (β-crystalline Form)

The β-crystalline thifluzamide obtained in Example 1 was ground in a jet mill (A-O Jet Mill, manufactured by Seishin Kigyo K.K.). This ground material 2.0 parts, sodium lignin sulfonate 5.0 parts, sodium alkylbenzenesulfonate 0.5 part, sodium polyacrylate 1.0 part, sodium tripolyphosphate 2.0 parts, bentonite 40 parts, calcium carbonate 49.5 parts, and water 16 parts were blended in an Almighty Mixer (manufactured by Dalton K.K.), and it was pelletized with an extruder type pelletizer equipped with a screen having 0.8 mm aperture (BR-200, manufactured by Fuji Powdal K.K.). This pellet was dried at 50° C., to obtain Pellet 1 (β-crystalline form).

Example 6
Pellet 2 (α+β crystals)

Thifluzamide (α-crystal) 35 parts obtained in the Referential Example and the thifluzamide (β-crystal) 65 parts obtained in Example 1 were mixed and ground in a jet mill (A-O Jet Mill). This ground thifluzamide showed an endothermic peak of 0.7 cal/g in the vicinity of 161° and an endothermic peak of 9.1 cal/g in the vicinity of 178° C. And, the X-ray diffraction analysis confirmed it to be a mixture of α-crystal and β-crystal. This ground thifluzamide (α-crystal:β-crystal=35:65) 2.0 parts was processed as in Example 5, to obtain Pellet 2 (mixture of α+β crystals).

Example 7
Pellet 3 (β-crystal)

Procedure of Example 5 was applied on 2.0 parts of the jet-milled thifluzamide (β-crystal) obtained in Example 2, to obtain Pellet 3 (β-crystal).

Example 8
Pellet 4 (α+β crystals)

Procedure of Example 5 was applied on 2.0 parts of the jet-milled thifluzamide (mixture of α+β crystals) obtained in Example 3, to obtain Pellet 4 (mixture of α+β crystals).

Example 9
Pellet 5 (α+β crystals)

Procedure of Example 5 was applied on 2.0 parts of the jet-milled thifluzamide (mixture of α+β crystals) obtained in Example 4, to obtain Pellet 5 (mixture of α+β crystals).

Comparative Example
Comparative Pellet (α-crystal)

Procedure of Example 5 was applied on 2.0 parts of the jet-milled thifluzamide (α-crystal) obtained in the Referential Example, to obtain Comparative Pellet (α-crystal).

Example of Test 1
Releasing Test of Pellets

Forty five milligrams each of the Pellets 1–5 and Comparative Pellet were added in a beaker containing hard water (hardness=10°) 1000 ml and kept at water temperature of 30° C. After standing calmly for 7 days, a portion of the solution was taken out from the center portion of the beaker, and content of thifluzamide was analyzed. Percent of thifluzamide being released was calculated by the following equation.

$$\% \text{ Released} = A \times 100 / B$$

A: Amount (mg) of thifluzamide released in water

B: Content (mg) of thifluzamide in the pellet which was added to the beaker

Results are presented in Table 1.

Example of Test 2
Test of Biological Effect

The are pot (1/10000 are size) containing the rice plants at its eighth leaf stage was treated with Pellet 1 or Comparative Pellet at a dose of 300 g/are. Seven days after the treatment, rice sheath blight which was cultured ahead of time on rice hull media was wrapped in cheese cloth and inserted between the stands of rice plants in the 1/10000 apot to inoculate the fungus.

After inoculation, the rice plants in the 1/10000 are pot were kept in a green house at 25° C. and a humidity of 100%. Seven days after the inoculation, height of the highest spot reached by the pest to cause disease was measured from the point of inoculation, and this was used to calculate the percent disease control. Results are shown in Table 1.

TABLE 1

|  | Thifluzamide being released, on the 7th day % | Rice leaf sheath blight percent disease control, inoculated on the 7th day after treatment % |
|---|---|---|
| Pellet 1 (β-crystal) | 100 | 82 |
| Pellet 2 (α + β crystals) | 80 | — |

TABLE 1-continued

| | Thifluzamide being released, on the 7th day % | Rice leaf sheath blight percent disease control, inoculated on the 7th day after treatment % |
|---|---|---|
| Pellet 3 (β crystal) | 100 | — |
| Pellet 4 (α + β crystals) | 70 | — |
| Pellet 5 (α + β crystals) | 80 | — |
| Comparative pellet (α-crystal) | 58 | 60 |

INDUSTRIALLY APPLICABILITY

Rate of release of thifluzamide in water can be enhanced by using the thifluzamide of the present invention which has been transformed the crystalline form as its effective ingredient of the pesticide composition, and thus it can improve the efficacy as a pesticide.

We claim:

1. Thifluzamide showing an endothermic peak at 175–180° C. when measured by differential scanning calorimeter analysis and having no other peak at less than that temperature.

2. Thifluzamide showing a peak at 2θ=17.68, 20.04, 23.04, 28.88 and 29.52 when measured by powder X-ray diffraction analysis.

3. A process for preparing thifluzamide of claim 1 comprising admixing a solution of thifluzamide dissolved in organic solvent with water to crystallize thifluzamide.

4. A process of claim 3 comprising incorporating the solution of thifluzamide dissolved in organic solvent into water to crystallize thifluzamide.

5. A process of claim 3 comprising incorporating water into the solution of thifluzamide dissolved in organic solvent to crystallize thifluzamide.

6. A process of claim 3, wherein the water solubility of the organic solvent at 20° C. is 10 or more parts by weight of water solution.

7. A process of claim 3, wherein the organic solvent is miscible with water in any ratio.

8. A process of claim 3, wherein the organic solvent is one or more solvents selected from the group consisting of alcohols, ketones, ethers, esters, nitrites, N-alkyl pyrrolidones, N,N-dimethylformamide and dimethylsulfoxide.

9. A pesticide composition containing the thifluzamide of claim 1 as its effective ingredient.

10. A pesticide composition containing thifluzamide prepared by the process of claim 3, as its effective ingredient.

11. A process for preparing thifluzamide of claim 2, comprising admixing a solution of thifluzamide dissolved in organic solvent with water to crystallize thifluzamide.

12. A process of claim 4, wherein the water solubility of the organic solvent at 20° C. is 10 or more parts by weight of water solution.

13. A process of claim 5, wherein the water solubility of the organic solvent at 20° C. is 10 or more parts by weight of water solution.

14. A process of claim 4, wherein the organic solvent is miscible with water in any ratio.

15. A process of claim 5, wherein the organic solvent is miscible with water in any ratio.

16. A process of claim 4, wherein the organic solvent is one or more solvents selected from the group consisting of alcohols, ketones, ethers, esters, nitrites, N-alkyl pyrrolidones, N,N-dimethylformamide, and dimethylsulfoxide.

17. A process of claim 5, wherein the organic solvent is one or more solvents selected from the group consisting of alcohols, ketones, ethers, esters, nitrites, N-alkyl pyrrolidones, N,N-dimethylformamide, and dimethylsulfoxide.

18. A pesticide composition containing the thifluzamide of claim 2 as its effective ingredient.

19. A pesticide composition containing thifluzamide prepared by the process of claim 4 as its effective ingredient.

20. A pesticide composition containing thifluzamide prepared by the process of claim 5 as its effective ingredient.

* * * * *